United States Patent
Thomas

(10) Patent No.: US 10,076,469 B2
(45) Date of Patent: Sep. 18, 2018

(54) TUBE MANAGEMENT SYSTEM

(71) Applicant: Casey James Thomas, Jackson, WY (US)

(72) Inventor: Casey James Thomas, Jackson, WY (US)

(*) Notice: Subject to any disclaimer, the term of this patent is extended or adjusted under 35 U.S.C. 154(b) by 90 days.

(21) Appl. No.: 14/851,488

(22) Filed: Sep. 11, 2015

(65) Prior Publication Data

US 2016/0074285 A1    Mar. 17, 2016

Related U.S. Application Data

(60) Provisional application No. 62/051,116, filed on Sep. 16, 2014.

(51) Int. Cl.
| | | |
|---|---|---|
| *A61J 15/00* | (2006.01) | |
| *A61M 25/02* | (2006.01) | |
| *A61M 16/04* | (2006.01) | |

(52) U.S. Cl.
CPC ....... *A61J 15/0053* (2013.01); *A61J 15/0061* (2013.01); *A61M 16/0497* (2013.01); *A61M 25/02* (2013.01); *A61M 2025/024* (2013.01); *A61M 2025/028* (2013.01); *A61M 2025/0286* (2013.01)

(58) Field of Classification Search
CPC .. A61J 15/0053; A61J 15/0061; A61M 25/02; A61M 2025/024; A61M 2025/0286; A61M 2025/028; A61M 2025/0293; A61M 16/0497
See application file for complete search history.

(56) References Cited

U.S. PATENT DOCUMENTS

| | | | | |
|---|---|---|---|---|
| 4,392,854 A | * | 7/1983 | Ibach | A61M 25/02 128/DIG. 26 |
| 4,699,616 A | * | 10/1987 | Nowak | A61M 25/02 128/DIG. 26 |
| 4,932,943 A | * | 6/1990 | Nowak | A61M 25/02 128/DIG. 26 |
| 5,026,352 A | * | 6/1991 | Anderson | A61M 16/0488 128/207.17 |
| 5,352,211 A | * | 10/1994 | Merskelly | A61M 25/02 128/DIG. 26 |
| 6,254,642 B1 | | 7/2001 | Taylor | |
| 7,063,088 B1 | * | 6/2006 | Christopher | A61M 16/0488 128/207.14 |

(Continued)

FOREIGN PATENT DOCUMENTS

| | | | | |
|---|---|---|---|---|
| WO | WO 2014031860 A1 | * | 2/2014 | A61M 25/02 |

OTHER PUBLICATIONS

ISA/US, International Search Report and Written Opinion issued on PCT application No. US2015/049930, dated Dec. 10, 2015, 7 pages.

*Primary Examiner* — Nathan R Price
*Assistant Examiner* — Courtney Fredrickson
(74) *Attorney, Agent, or Firm* — Greenberg Traurig, LLP

(57) ABSTRACT

A tube management system has a tube receiving element, a base element, and attachment elements extending from the base element. The tube receiving element is provided with a gripping element that functions to prevent tube migration. The attachment elements are provided within openings for receiving a device which is used to secure the tube management system to a patient.

6 Claims, 8 Drawing Sheets

(56) References Cited

U.S. PATENT DOCUMENTS

| | | |
|---|---|---|
| 2006/0025723 A1* | 2/2006 | Ballarini ............... A61M 25/02 604/180 |
| 2007/0088280 A1* | 4/2007 | Gomez ................. A61M 25/02 604/174 |
| 2008/0051703 A1 | 2/2008 | Thornton et al. |
| 2010/0305403 A1 | 12/2010 | Bartlett et al. |
| 2013/0218174 A1 | 8/2013 | Bjerken |

* cited by examiner

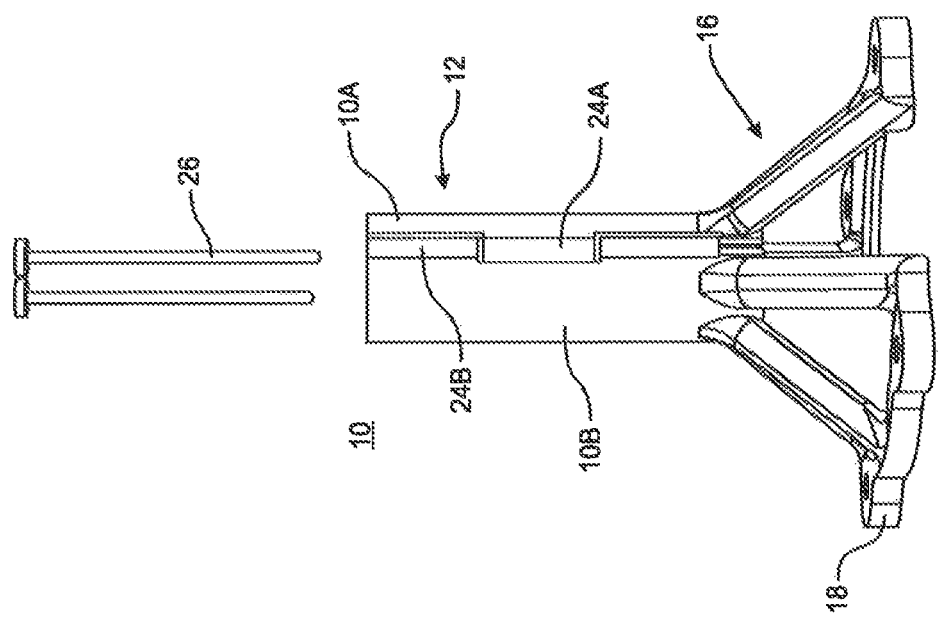

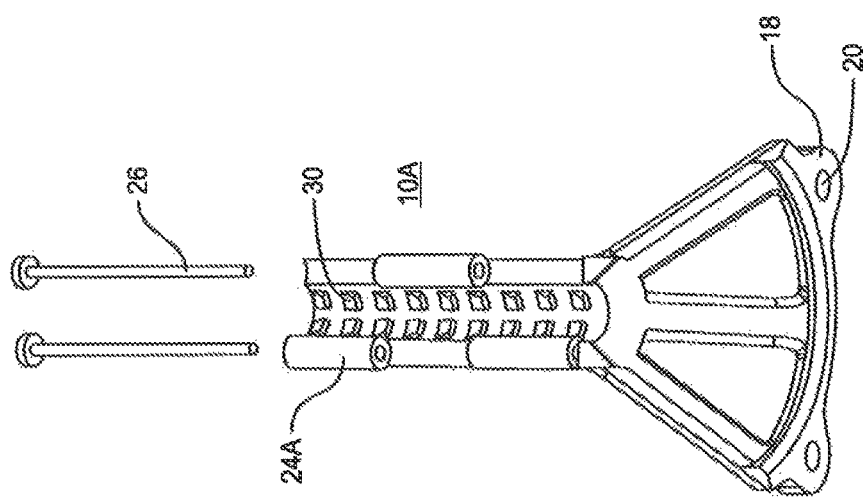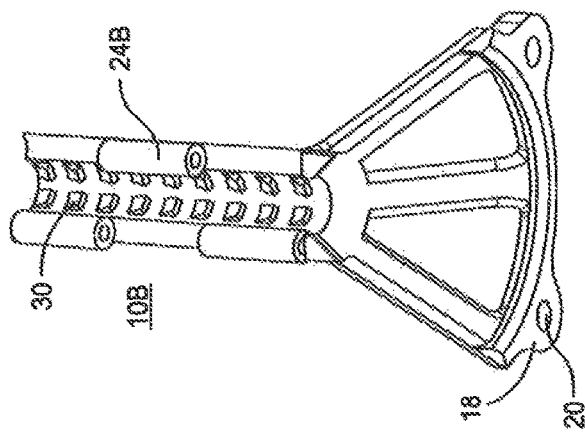

TUBE MANAGEMENT SYSTEM

RELATED APPLICATION INFORMATION

This application claims the benefit of U.S. 62/051,116, filed on Sep. 16, 2014, the disclosure of which is incorporated herein by reference in its entirety.

BACKGROUND

The following generally relates to systems and methods for securing a tube, such as a feeding tube, to a patient.

Patients who cannot take nutrition orally need another form of access to the gastrointestinal tract (GI). The following list are some of the potential situations where a person would not be able to eat normally: old age, disruption of the normal swallowing mechanism, neurologic diseases, cancers of the GI tract, prolonged ventilator dependence, trauma, stroke. For short term nourishment, tubes can be placed through the mouth or nose into the stomach or small bowel for feeding, however, this is a short-term solution. For longer access, tubes may be placed directly through the abdominal wall and into the stomach or jejunum (small bowel). These tubes can be placed via an open technique where an incision is made in the abdominal wall and the stomach or bowel is opened and the tube is placed directly into the lumen.

Still further, a feeding tube system, such as a Percutaneous Endoscopically placed Gastrostomy (PEG) tube system, can be used for this purpose. When such a system is used, an endoscope is placed down the esophagus and into the stomach. A needle is then placed through the abdominal wall into the stomach under direct visualization via the endoscope. Guide wires and dilators are then used to place a tube into the stomach. The tension of the tube holds the stomach against the abdominal wall and eventually a tract forms. Nutrition can then be instilled via the tube directly into the stomach. However, the complication rate for this procedure is high and the literature states that it is between 10-30%. Usually the complication is simply a wound infection, but not uncommonly the tube can become dislodged and spill the feeding material into the abdominal cavity resulting in catastrophic morbidity. Thus, currently known feeding tube systems are seen to be inadequate to prevent these complications because the bumper that is utilized with such currently known feeding tube systems allows the tube to slide. These complications not only result in increased patient morbidity and mortality, but also drastically increased medical costs.

SUMMARY

To address the inadequacies of currently known feeding tube systems, the following describes a tube management system that functions to securely hold a feeding tube and to prevent any feeding tube migration. Generally, the tube management system comprises a tube holding element that is dimensioned slightly larger than a feeding tube that is to be placed there within. To prevent tube migration, the interior of the tube holding element may be provided within one or more gripping elements. The one or more gripping elements may take the form of a plurality of protuberances that are formed on the interior wall of the cylindrical element where the protuberances are sized to grip into the wall of the tube without penetrating through the wall of the tube. The one or more gripping elements may alternatively be in the form of moveable elements that will function to tighten against (or move into) the tube in response to any movement of the tube. To secure the tube management system to the patient, the tube holding element may additionally be provided with a generally domed shaped base element that is dimensioned to sit over the bumper that is a part of existing feeding tube systems. The base element has extending therefrom a plurality of attachment elements wherein each of the plurality of attachment elements has an opening by which the tube management system can be attached to the abdominal wall using an appropriate attachment element, such as sutures. In a preferred embodiment, the tube management system comprises two complimentary pieces which, when assembled together, provide the aforementioned tube holding element, base element, and attachment elements. In this manner, the tube management system can be assembled over the feeding tube prior to its attachment to the patient.

A better understanding of the objects, advantages, features, properties and relationships of the subject tube management system will be obtained from the following detailed description and accompanying drawings which set forth illustrative embodiments and which are indicative of the various ways in which the principles of the hereinafter claimed invention may be employed.

BRIEF DESCRIPTION OF THE DRAWINGS

For a better understanding of the various aspects of the subject tube management system reference may be had to the attached drawings in which:

FIG. 1 illustrates an exemplary tube management system constructed in accordance with the description which follows;

FIG. 2 illustrates the tube management system of FIG. 1 in a state prior to assembly;

DETAILED DESCRIPTION

Figure 4:
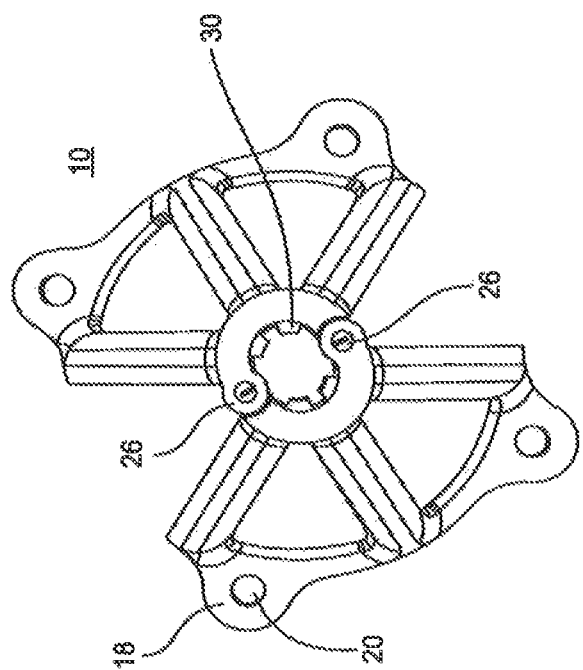
FIG. 4 illustrates a top view of the assemble tube management system of FIG. 1.
Figure 3:
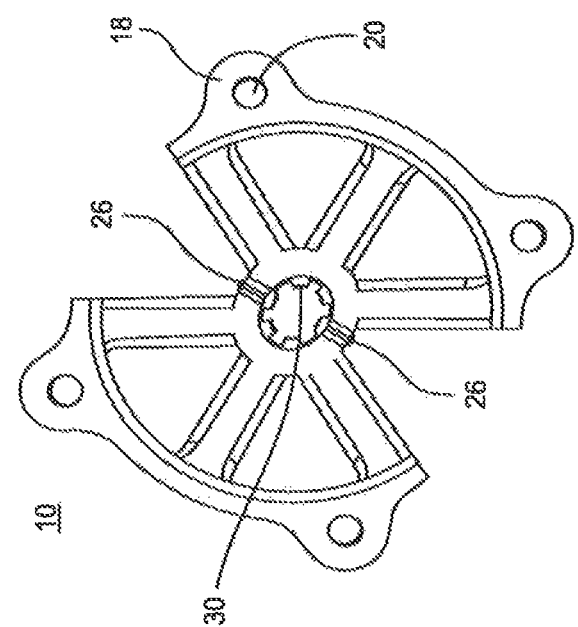
FIG. 3 illustrates a bottom view of the assembled tube management system of FIG. 1.
Figure 5:
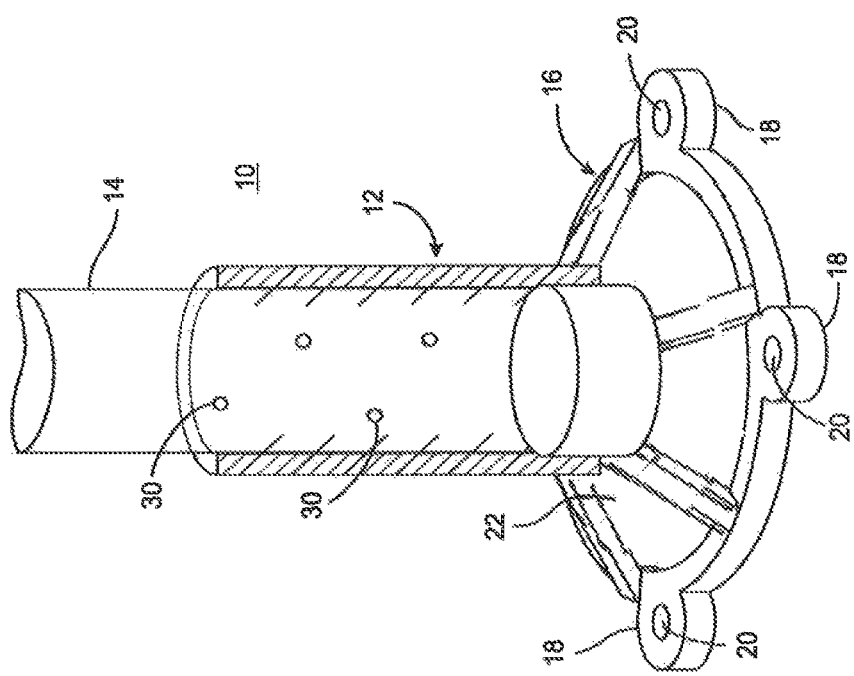
FIG. 5 illustrates the tube management system of FIG. 1 as secured to a patient.

Turning now to the figures wherein like reference numerals refer to like elements, hereinafter is described an exemplary tube management system 10. Generally, the tube management system 10 comprises a tube holding element 12, which is preferably cylindrical in shape, which is to be placed about a feeding tube 14. The tube holding element 12 has a generally dome shaped base portion 16 from which extends a plurality of attachment elements 18. Each of the plurality of attachment elements 18 includes an opening 20 for receiving an attachment device, such as a suture or the like, by which the tube management system 10 is to be attached to a patient. While the illustrated base portion 16 will form a complete unit about the lower end of the tube holding element 12, it will be appreciated that the base portion 16 can comprise one or more discrete elements that can be spaced around the end of the tube holding element 12 as desired. In any configuration, it is preferred that the base portion 16 be sized to accommodate there within a bumper 22 (shown in FIG. 5) that is a known component of existing feeding tube systems. Similarly, while the illustrated base portion has four, spaced attachment elements 18, it will be appreciated that any number of attachment elements 18 can be provided to the tube management system 10 so long as the number of attachment elements 18 allows the tube management system 10 to be securely attached to a patient over the bumper 22.

As the tube management system 10 is contemplated for use with tubes of various sizes, the particular dimensions that are provided to the tube holding element 12 (and the additional components) may vary according to need. Preferably, the tube holding element 12 is provided with an interior dimension that is slightly larger than the feeding tube 14 that is to be placed there within. When used with a conventional feeding tube 14, the overall height of the tube management system 10 may be approximately 2 inches while the width across the base element 16 and attachment elements 18 may be approximately 2 inches.

In a preferred embodiment, the tube management system 10 comprises two complimentary pieces 10A and 10B which, when assembled together, provide the aforementioned tube holding element 12, base element 16, and attachment elements 18. In this manner, the tube management system 10 can be assembled over the feeding tube 14 prior to its attachment to the patient. In an exemplary embodiment, the complimentary pieces 10A and 10B are provided with respective, cooperating dovetail-style joint elements 24A and 24B which are arranged to be aligned with one another when the complimentary pieces 10A and 10B are brought together. The joint elements 24A and 24 may be provided with alignable openings into which a pin 26 may be inserted to hold the complimentary pieces 10A and 10B together. In this example, the pin 26 may also be removed from the openings to allow the complimentary pieces 10A and 10 to be separated and easily removed from the tube 14 when no longer needed. It will also be understood that it some instances it may be desired to have the complimentary pieces 10A and 10B permanently adjoined together upon the tube 14 and, to this end, any know technique may be used. Similarly, it is to be understood that alternative devices and techniques may be used to removably secure the complimentary pieces 10A and 10B with one another. While the complimentary pieces 10A and 10B are each preferably molded from a plastic material as respective unitary components, it will be appreciate the various elements can be separately molded and joined together as desired and/or that other materials can be used as necessary for any particular application.

Figure 7:
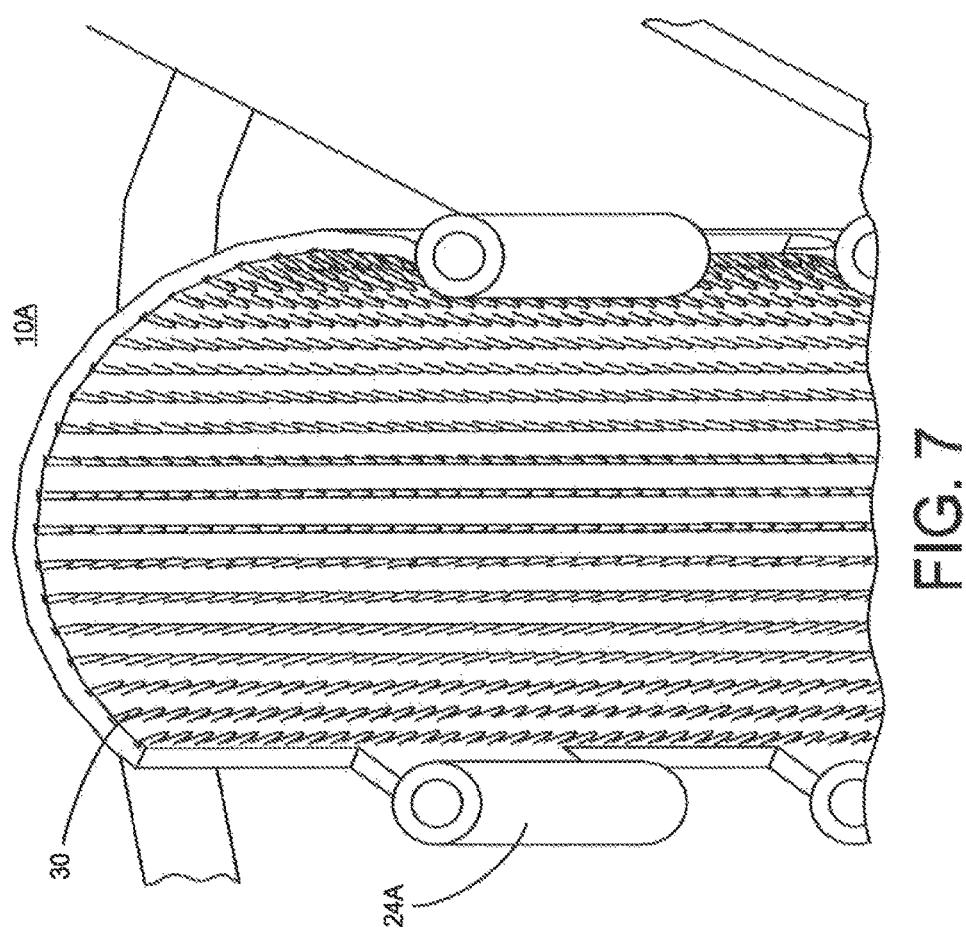
FIGS. 7-10 illustrate exemplary gripping elements for use in connection with the tube management system of FIG. 1.
Figure 8:
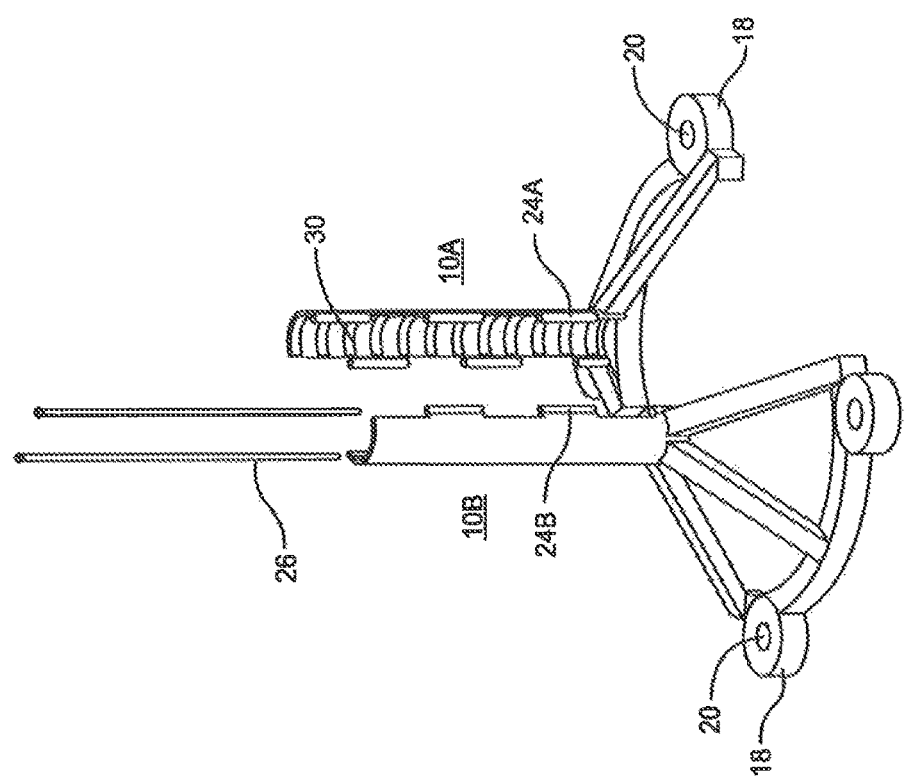
Figure 10:
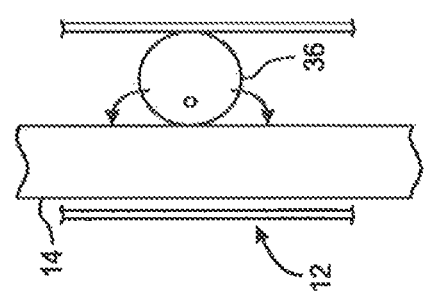
Figure 9:
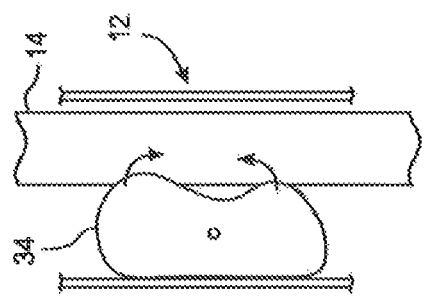

To prevent tube migration, the interior of the tube holding element 12 may be provided within one or more gripping elements. The one or more gripping elements may take the form of a plurality of protuberances 30 that are formed on and spaced about the interior wall of the cylindrical element 12. Preferably, the protuberances 30 are sized to grip into the wall of the tube 20 without penetrating through the wall of the tube 14. In one example, the gripping elements 30 are provided with surfaces that function to inhibit removal of the tube 20 while allowing the tube to be moved downwardly (towards the patient) as particularly shown in FIG. 2. In another example, the gripping elements 30 are in the form of teeth as shown in FIG. 7. In yet another example, the gripping elements 30 are in the form of protuberances having squared edges as shown in FIG. 8. In yet further examples, the one or more gripping elements may be in the form of moveable elements that will function to tighten against (or move into) the tube 14 in response to any movement of the tube 14 relative thereto. By way of non-limiting example, the moveable elements may comprise a rocker-like element 34 that would be pivotally attached to the interior surface of the tube holding element 12 as illustrated in FIG. 9. As will be appreciated, the rocker-like element 34 can be provided with cam surfaces that would be placed into engagement with the tube 14. A slight movement of the tube 14 relative to the rocker-like element 34 will then cause the rocker-like element 34 to responsively move about its pivot attachment whereupon a one of the cam surfaces will be driven into the wall of the tube 14 and further movement of the tube 14 in that same direction will be inhibited. In a similar manner, the moveable element may comprise a ball-like element 36 that would be rotationally attached via use of an off center axle to the interior surface of the tube holding element 12 as shown in FIG. 10. The surface of the ball-like element 36 would also be placed into engagement with the tube 14 such that a slight movement of the tube 14 relative to the ball-like element 36 will cause the ball-like element 36 to responsively rotate whereupon the thicker part of the ball-like element 36 will be driven into the wall of the tube 14 and further movement of the tube 14 in that same direction will be inhibited.

Figure 6:
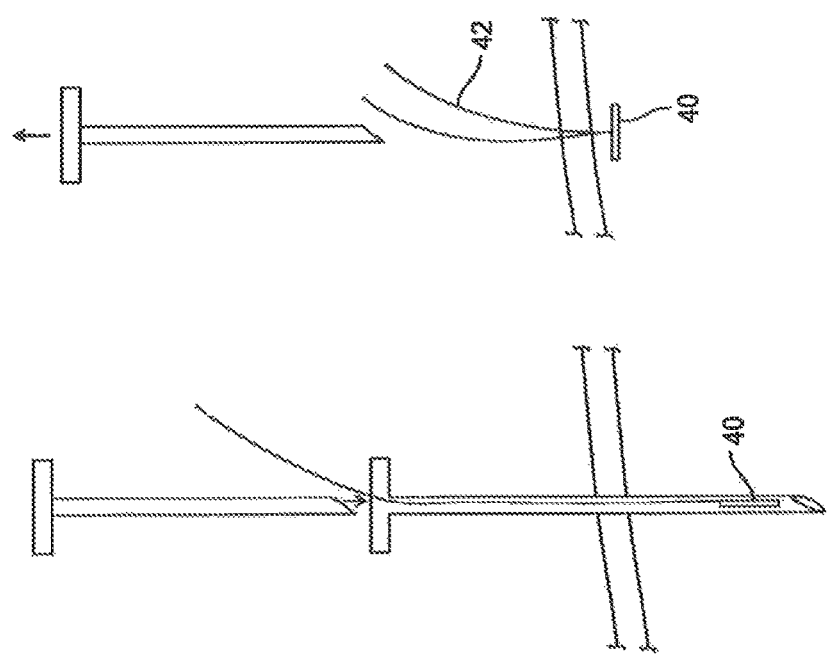
FIG. 6 illustrates an exemplary method for preparing for the securement of the tube management system of FIG. 1 to the patient.

Turing now to FIG. 6, it is contemplated that tube management system 10 will be secured transabdominally with T-fasteners 40 which are commercially available. The T-fasteners 40 will be placed under direct vision with an endoscope in the stomach. When the sutures of the T-fasteners 40 are passed through the holding elements 18 of the tube management system, a fixed unit will be created consisting of the stomach (or bowel), the abdominal wall, the feeding tube 14, and the tube management system 10. This assemblage will eliminate any sliding of the tube 14 and the potential for spillage of feeding material into the abdominal cavity.

While various concepts have been described in detail, it will be appreciated by those skilled in the art that various modifications and alternatives to those concepts could be developed in light of the overall teachings of the disclosure. For example, while described in the context of a feeding tube management system, it will be appreciated that a device of the general type described could be used to secure any tube that has transabdominal, enteral access (i.e., any tube that is placed through the abdominal wall into any portion of the GI tract—stomach, small or large bowel). Similarly a device of the general type described could be used to secure tubes that are placed through the nose or mouth into the stomach for feeding or venting. Accordingly, the particular concepts disclosed herein are meant to be illustrative only and not limiting as to the scope of the invention which is to be given the full breadth of the appended claims and any equivalents thereof.

What is claimed is:

1. A tube management system for use with a tube, comprising:

a tube receiving element into which the tube is to be positioned, wherein the tube receiving element has a first portion having a first portion interior surface and a first portion exterior surface and a second portion having a second portion interior surface and a second portion exterior surface, wherein a first side of the first portion is hingedly connected to a first side of the second portion, and wherein a second side of the first portion has a first portion edge and a second side of the second portion has a second portion edge that is complimentary to the first portion edge whereby, when the first portion edge of the second side of the first portion is moved to a position that is adjacent to the second portion edge of the second side of the second portion the first portion interior surface and the second portion interior surface function to provide the tube receiving element with a generally cylindrical interior surface and the first portion exterior surface and the second portion exterior surface function to provide the tube receiving element with a generally cylindrical exterior surface;

a first plurality of holding elements and a second plurality of holding elements, wherein the first plurality of holding elements are cooperable with the second plurality of holding elements to maintain the first portion edge of the second side of the first portion in the position that is adjacent to the second portion edge of the second side of the second portion and wherein the first plurality of holding elements are spaced from each other and arranged in a line that is generally parallel to a central axis of the generally cylindrical interior surface and the second plurality of holding elements are spaced from each other and arranged in a line that is generally parallel to the central axis of the generally cylindrical interior surface, and wherein each of the first plurality of holding elements and each of the second plurality of holding elements have an opening and wherein the openings are alignable to receive a pin to maintain the first portion edge of the second side of the first portion in the position that is adjacent to the second portion edge of the second side of the second portion;

a base element coupled to a lower edge of the tube receiving element wherein the base element comprises a plurality of openings each for accepting a device that is used to secure the tube management system to a patient; and a gripping feature associated with an interior surface of the tube receiving element to prevent migration of the tube when the tube is positioned there within.

2. The tube management system as recited in claim 1, wherein the plurality of openings are each sized to receive sutures.

3. The tube management system as recited in claim 1, wherein the gripping feature comprises a plurality of protuberances formed on and spaced about the interior surface of the tube receiving element, the protuberances being sized to dig into a wall of the tube when the tube is positioned there within without piercing the wall of the tube.

4. The tube management system as recited in claim 1, wherein the gripping feature comprises a rocker-like element that is pivotally mounted to the interior surface of the tube receiving element, the rocker-like element having surfaces that will be pivoted into a wall of the tube in response to a corresponding movement of the tube when positioned there within.

5. The tube management system as recited in claim 1, wherein the gripping feature comprises a ball-like element that is rotationally offset mounted to the interior surface of the tube receiving element, the ball-like having surfaces that will be rotated into a wall of the tube in response to a corresponding movement of the tube when positioned there within.

6. The tube management system as recited in claim 1, wherein the first plurality of holding elements and the second plurality of holding elements are generally disposed between the generally cylindrical interior surface and the generally cylindrical exterior surface when the first portion edge of the second side of the first portion is in the position that is adjacent to the second portion edge of the second side of the second portion.

* * * * *